US009387306B2

(12) United States Patent (10) Patent No.: US 9,387,306 B2
Andreae et al. (45) Date of Patent: Jul. 12, 2016

(54) UNIVERSAL CATHETER SECUREMENT DEVICE

(71) Applicants: Andrew Eric Andreae, Orlando, FL (US); Lena Mona Badr, Manassas, VA (US); James Andrew Bonaffini, Warrenton, VA (US); Benjamin Ray Campbell, Atlanta, GA (US); Darian Anthony Edwards, Springfield, VA (US); Ilya Gurin, Philadelphia, PA (US); Angela Leslie-Anne Jividen, Manassas, VA (US); Lydia An Luu, Fairfax, VA (US); John Christian McMichael, Clarksville, MD (US); Matthew Thomas Rhoads, Alexandria, VA (US); Zi Ye, Charlottesville, VA (US); Sibo Zhang, Virginia Beach, VA (US)

(72) Inventors: Andrew Eric Andreae, Orlando, FL (US); Lena Mona Badr, Manassas, VA (US); James Andrew Bonaffini, Warrenton, VA (US); Benjamin Ray Campbell, Atlanta, GA (US); Darian Anthony Edwards, Springfield, VA (US); Ilya Gurin, Philadelphia, PA (US); Angela Leslie-Anne Jividen, Manassas, VA (US); Lydia An Luu, Fairfax, VA (US); John Christian McMichael, Clarksville, MD (US); Matthew Thomas Rhoads, Alexandria, VA (US); Zi Ye, Charlottesville, VA (US); Sibo Zhang, Virginia Beach, VA (US)

(*) Notice: Subject to any disclaimer, the term of this patent is extended or adjusted under 35 U.S.C. 154(b) by 177 days.

(21) Appl. No.: 14/271,408

(22) Filed: May 6, 2014

(65) Prior Publication Data

US 2014/0350474 A1 Nov. 27, 2014

Related U.S. Application Data

(60) Provisional application No. 61/820,624, filed on May 7, 2013.

(51) Int. Cl.
*A61M 25/02* (2006.01)

(52) U.S. Cl.
CPC .......... *A61M 25/02* (2013.01); *A61M 2025/026* (2013.01); *A61M 2025/028* (2013.01); *A61M 2025/0213* (2013.01)

(58) Field of Classification Search
CPC .......... A61M 25/02; A61M 2025/026; A61M 2025/0213; A61M 2025/028
USPC ........................................................ 604/174
See application file for complete search history.

(56) References Cited

U.S. PATENT DOCUMENTS 5,131,412 A * 7/1992 Rankin ................. A61F 5/3761
128/869

* cited by examiner

*Primary Examiner* — Theodore Stigell
*Assistant Examiner* — Amber Stiles

(57) ABSTRACT

An intravenous catheter securement device comprises of an intravenous catheter board stabilizer that conforms to patients' bodies and an adjustable elastic sleeve with a hole for catheter insertion, with two overlying flaps for catheter securement. The intravenous catheter board base has holes on either side, one side for connection of the elastic sleeve, and the other side provides a fastening location for elastic bands attached to the sleeve for tightness adjustment. An embodiment of the invention involving the intravenous board is displayed separately as an alternative innovation. This device is comprised of a simple form fitting elastic sleeve having a catheter opening with the intent of applying a removable adhesive to the sleeve itself over the catheter for securement purposes. These embodiments establish a simple, standardized, and safe method of securing intravenous catheters sans adhesive material in contact with the epidermis.

6 Claims, 7 Drawing Sheets

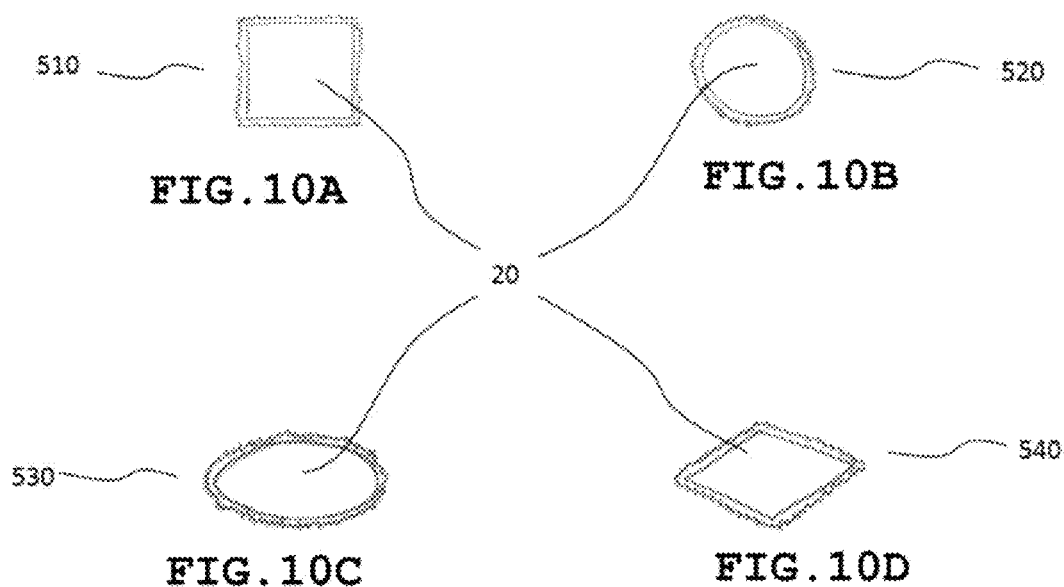
FIG. 10A  FIG. 10B
FIG. 10C  FIG. 10D
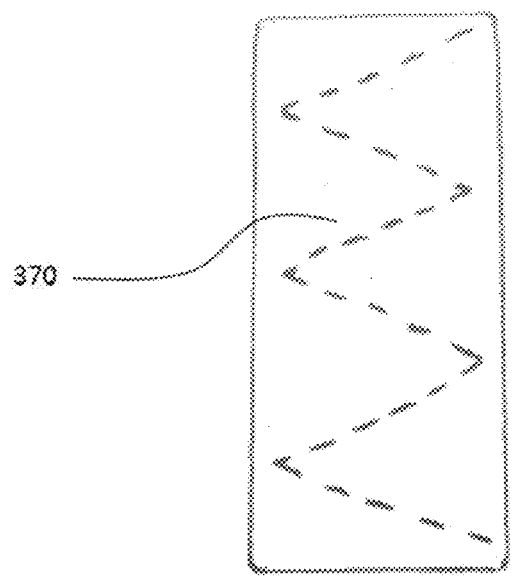
FIG. 11

UNIVERSAL CATHETER SECUREMENT DEVICE

FEDERALLY SPONSORED RESEARCH

Not Applicable

SEQUENCE LISTING OR PROGRAM

Not Applicable

BACKGROUND

1. Field of Invention

This invention relates to catheter securement devices, specifically in their use to stabilize intravenous catheters in clinical settings.

2. Description of Prior Art

More than 400,000 newborns are admitted to Neonatal Intensive Care Units (NICU) each year in the United States. Of these, a majority require long-term intravenous catheters to deliver necessary fluids and medicines. Many patients in NICUs are born considerably premature and have underdeveloped skin. A problem arises when traditional catheter securement devices damage underdeveloped skin and thus present a risk to neonates' health.

Traditional methods to secure catheters to patients require adhesives. It is common practice to lay multiple adhesive strips across the hub of the catheter and directly onto patients' skin adjacent to the site of entry. During a patient's stay, catheters are removed, cleaned, and re-attached periodically in patients requiring long-term intravenous tubes. This usually occurs once every two days, although specific routines vary by hospital.

Conventional catheter-anchoring methods have been used for nearly a century. While specific adhesive compounds have been changed to alter binding properties to the skin or to catheters, there have been no fundamental modifications to the solution. This method is generally effective in securement, but it fails to accommodate all the needs of the wide variety of patients admitted to hospitals. Its implementation on neonates is especially problematic.

Premature infants are underdeveloped in almost every way. Consequently, their skin is incredibly fragile and thin. The same tape-based securement methods used on adults are commonly used on NICU patients. Whereas the extent of adhesive-related damage in adults is generally moderate irritation, NICU patients face much more severe health issues. Their skin is so delicate that when tape is peeled away to change a catheter, the layer of skin in contact with the adhesive is often also peeled away. The resulting wounds are prone to infection, an obstacle that many premature infants' underdeveloped immune systems may not have the ability to overcome. There is clearly a pressing need for alternative catheter-securement methods or devices for NICU patients.

SUMMARY

The present invention has been developed in response to problems and needs in the art that have not yet been fully resolved by currently available universal catheter securement devices and methods. Thus, the following device, and method of application herein, establish a more effective alternative for securing an intravenous catheter to the skin without damage or otherwise harmful effects while ensuring effective catheter function for the duration of insertion.

An embodiment of the present invention provides an universal catheter securement device and related method for applying the device properly to the patient to prevent the use of adhesive materials or the movement, shearing, or displacement of the catheter once inserted in the patient. The present device promotes standardised, quick, and simple application of catheter securement free from any adhesive components in direct contact with the patient's skin. This innovation will improve skin care, the incidence of infection, nursing convenience, and intravenous catheter stability and therefore functions associated with intravenous' catheter application.

The ability to stabilize intravenous catheters sans adhesive contact with the skin is imperative in maintaining the integrity of skin upon application and removal of intravenous catheters, which leads to a lower incidence of skin deformation, tearing, or damage and therefore a lower rate of infection due to an intact epidermis barrier. The device herein established will provide a standardized and simple means of securing intravenous catheters without any damaging effects to the epidermis. This will improve patient comfort, care, and overall outcome.

DRAWING FIGURES

In the drawings, closely related figures have the same number but different alphabetic suffixes. These drawings only depict typical embodiments of the invention and are not intended to be considered the only possible embodiments or to limit the scope of the invention.

FIG. 1A-B shows the placement of an intravenous catheter board device on the arm of a patient according to a representative embodiment.

FIG. 2A-B shows a perspective view of an intravenous catheter board device according to a representative embodiment.

FIG. 3A-B shows a perspective view of the upper fabric open and closed flap assemblies according to a representative embodiment.

FIG. 10A-D shows a top view of the possible embodiments of the fabric cutout shapes.

FIG. 11 shows a top view of the sewing pattern used for discussed designs.

DETAILED DESCRIPTION

Figure 1A:
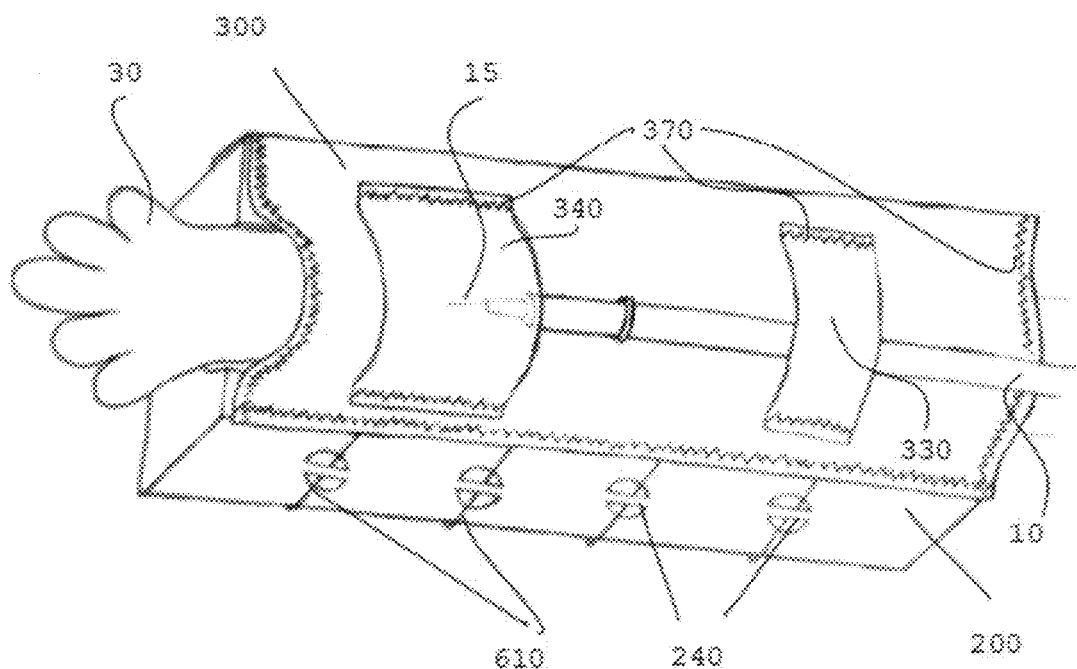

FIG. 1A represents the upper fabric assembly 300 attached to the intravenous catheter board base 200 secured on a patient's arm 30. The upper fabric assembly 300 shows the intravenous catheter tip securement flap 340 and intravenous catheter line securement flap 330 closed over the intravenous catheter tip 15 and intravenous catheter line 10. The elastic bands 610 are drawn taut through the cylindrical holes 240 on the intravenous catheter board base 200.

Figure 1B:
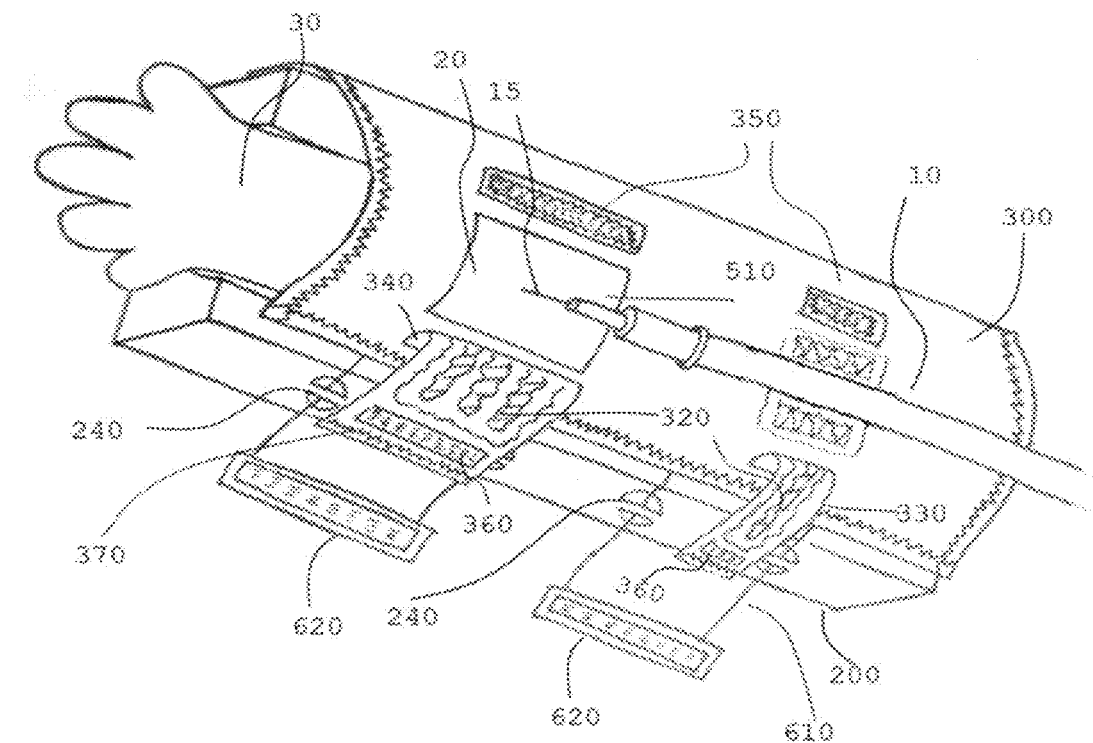

FIG. 1B represents the upper fabric assembly 300 attached to the intravenous catheter board base 200 resting on a patient's arm 30 not yet secured. The upper fabric assembly 300 shows the rectangle cutout 510 allowing for the insertion of the intravenous catheter tip 15. The intravenous catheter tip 15 is secured by the intravenous catheter tip securement flap 340 consisting of the loop Velcro 360 that is able to attach to another opposing hook Velcro 350 to cover the rectangle cutout 510. The flap is lined with non-slip material 320 to prevent movement of the intravenous catheter tip 15. The intravenous catheter line securement flap 330 is secured over the intravenous catheter line 10 for additional securement. The intravenous catheter line securement flap 330 consists of the loop Velcro 360 that is able to attach to the opposing hook Velcro 350. The second flap is also lined with non-slip material 320. For adjustability, elastic bands 610 are attached to the upper fabric assembly 300. The elastic bands 610, threaded through the cylindrical holes 240, are able to attach to the intravenous catheter board base Velcro 230.

Figure 2A:
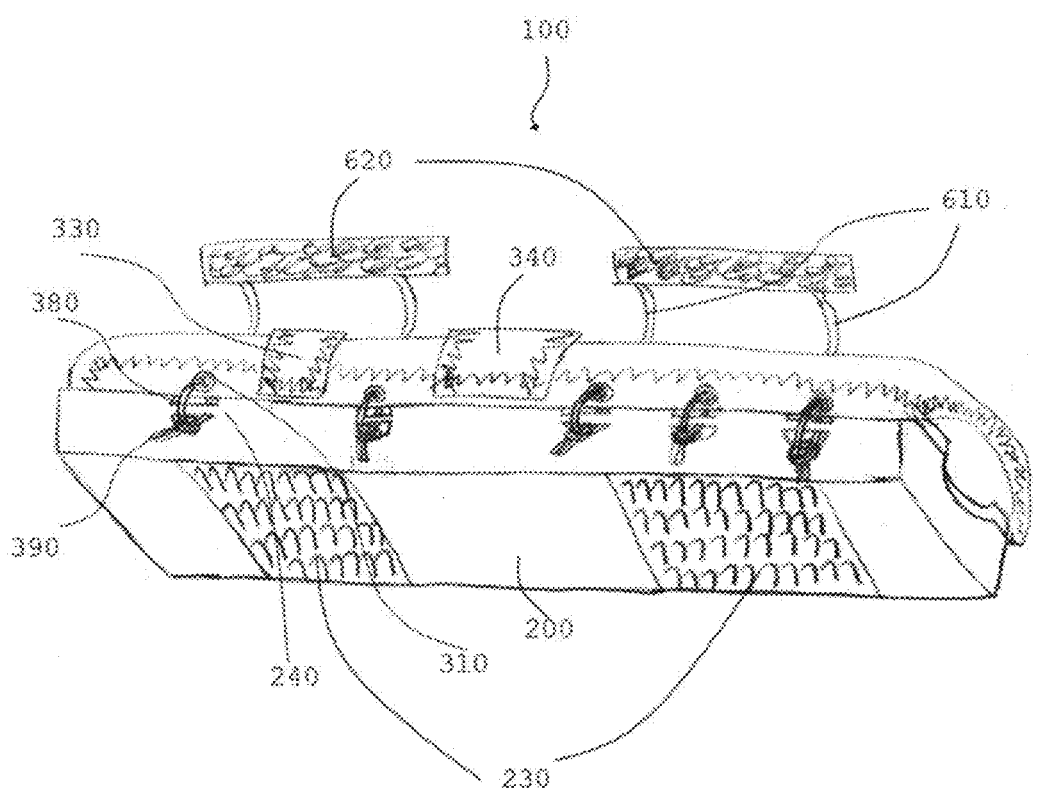
Figure 2B:
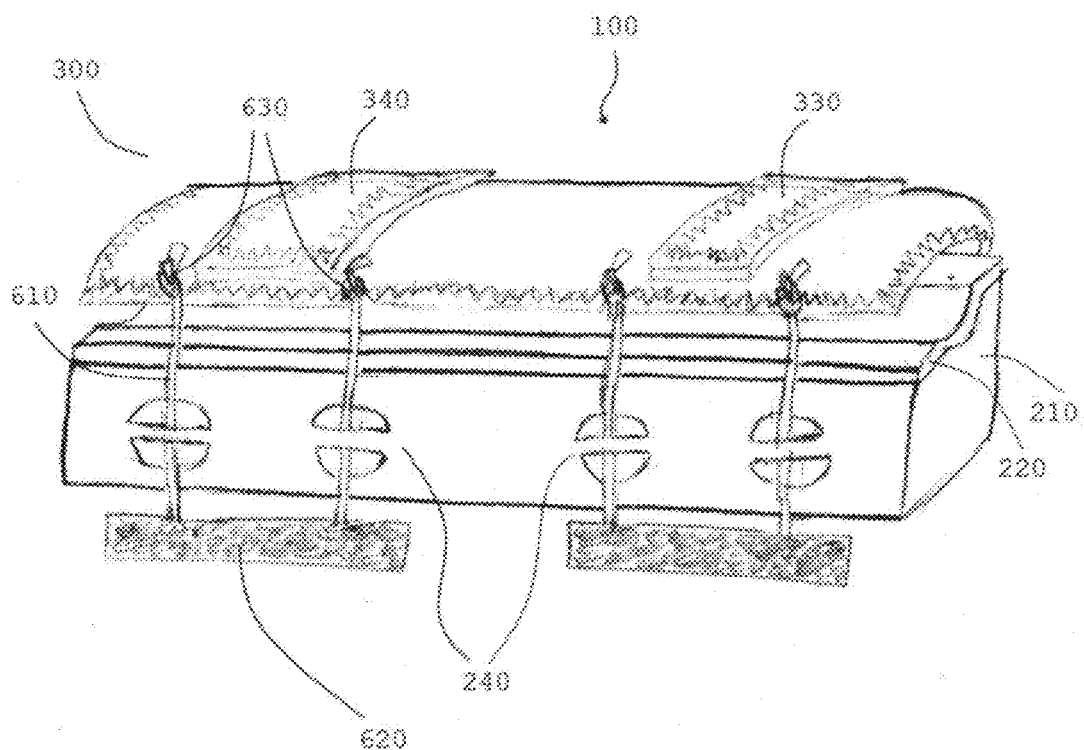

An embodiment of the design incorporating an intravenous catheter board base 200 is shown in FIG. 2A and FIG. 2B. The upper fabric assembly 300 may manifest itself in any of the variations of the design described earlier, with additional components necessary for the attachment of the upper fabric assembly 300 to the intravenous catheter board base 200 to form the complete intravenous catheter board device 100.

FIG. 2A represents a possible embodiment of the design from the side of the device where the upper fabric assembly 300 is permanently fastened to the intravenous catheter board base 200. The connection point on the board is comprised of cylindrical holes 240 on the side of the board. Non-elastic bands 380 are threaded through the cylindrical holes 240 and then through eyelet reinforced holes 310 on the upper fabric assembly 300. The non-elastic bands 380 are tied to form a double band knot 390 that forms a loop that permanently holds the upper fabric assembly 300 to the intravenous catheter board base 200. The non-elastic bands 380 may be any non-elastic, closed circle structure, either rigid or flexible, that can withhold enough force to facilitate the connection between the two portions of the device. FIG. 2A also shows the bottom of the intravenous catheter board base 200, containing two strips of intravenous catheter board base Velcro 230 where the tightening loop Velcro strips 620 attach to in order to tighten the intravenous catheter board device 100. In addition, a foam padding 220, which could be made of foam or any other soft material, may be placed on top of the intravenous catheter board base 200 to add comfort to the patient's arm.

FIG. 2B represents a possible embodiment of the intravenous catheter board device 100 from the opposite side than that of FIG. 3. Four elastic bands 610 are made into a single band knot 630 then stitched to the elastic fabric using the sewing pattern shown in FIG. 15. The other end of two adjacent elastic bands 610 are connected by a thin loop Velcro strip 620. The same is done for the other two elastic bands 610. The elastic bands 610 are threaded through the cylindrical holes 240 on the intravenous catheter board base 200.

Figure 3A:
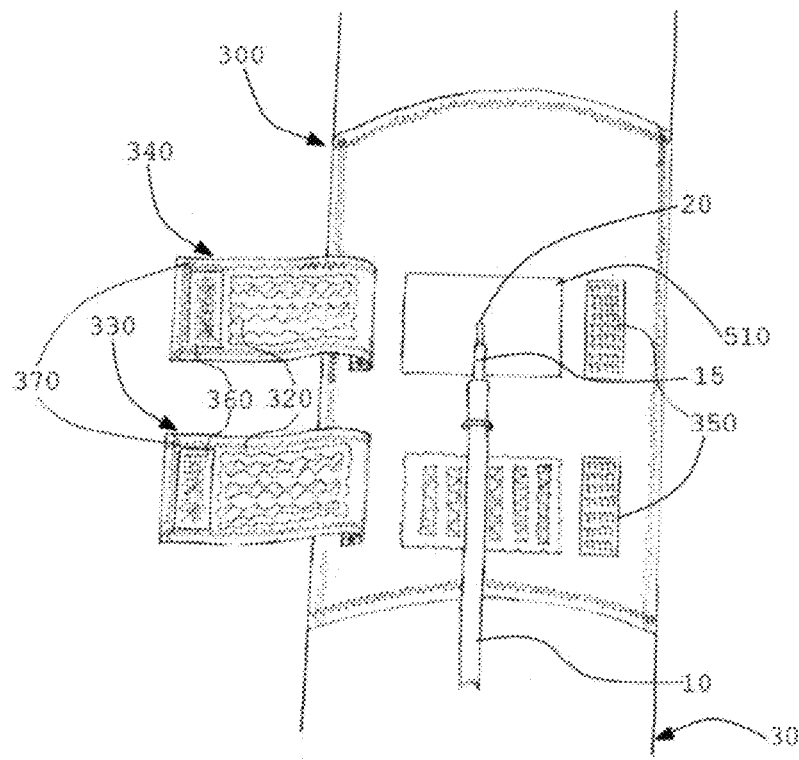
Figure 3B:
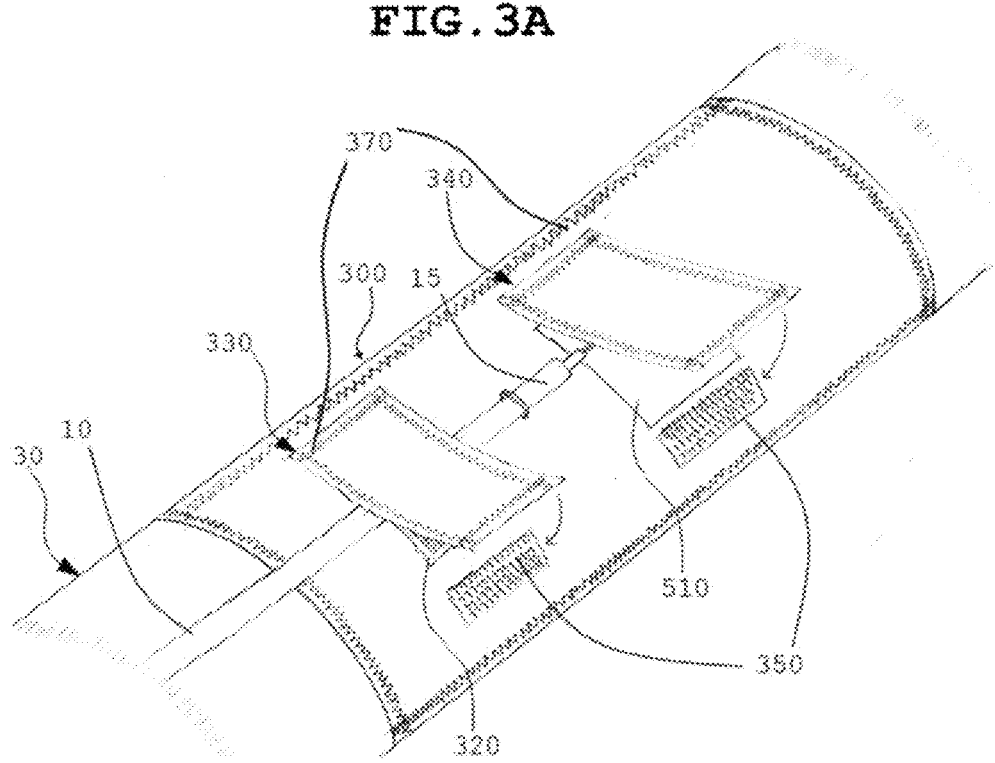

An embodiment of the upper fabric assembly 300 is represented in FIG. 3A, a perspective view of the open flap assembly, and FIG. 3B, a perspective view of the closed flap assembly. The upper fabric assembly 300 rests on a patient's arm 30 allows an intravenous catheter tip 15 to insert through a rectangle cutout 510 into a skin opening 20. An intravenous catheter tip securement flap 340 is attached to the upper fabric assembly 300 via elastic fabric stitches 370. The bottom side of the intravenous catheter tip securement flap 340 has non-slip material 320 attached by elastic fabric stitches 370 to prevent the intravenous catheter tip 15 from moving. The bottom side of the intravenous catheter tip securement flap 340 also has loop Velcro 360 attached by elastic fabric stitches 370 which will link to the hook Velcro 350 in order to close the intravenous catheter tip securement flap 340. An intravenous catheter line securement flap 330 is attached to the upper fabric assembly 300 via elastic fabric stitches 370. The bottom side of the intravenous catheter line securement flap 330 has non-slip material 320 attached by elastic fabric stitches 370 to prevent the catheter line from moving. The bottom side of the intravenous catheter line securement flap 330 also has loop Velcro 360 attached by elastic fabric stitches 370 which will link to the hook Velcro 350 in order to close the intravenous catheter line securement flap 330. There is also non-slip material 320 attached to the upper fabric assembly 300 via elastic fabric stitches 370 beneath the intravenous catheter line 10 to further prevent the movement of the intravenous catheter line 10.

Figure 4:
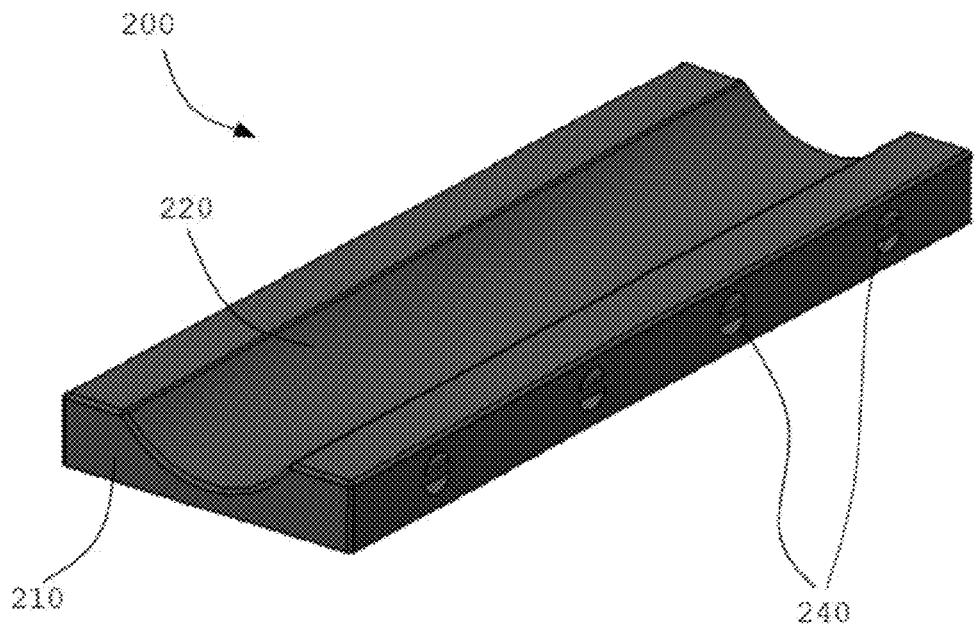
FIG. 4 shows a perspective view of an intravenous catheter board base according to a representative embodiment.

FIG. 4 is a representation of the intravenous catheter board base 200. The plastic board 210 has a cylindrical indentation which is covered with foam padding 220. The indentation is to allow the neonate's arm to rest on the intravenous board securely. The foam padding 220 is to allow for comfort of the neonate's arm and prevent any harsh surface from being in contact with the neonate's skin. The cylindrical holes 240 within the plastic board 210 are to allow for the attachment of the elastic bands 610.

Figure 5:
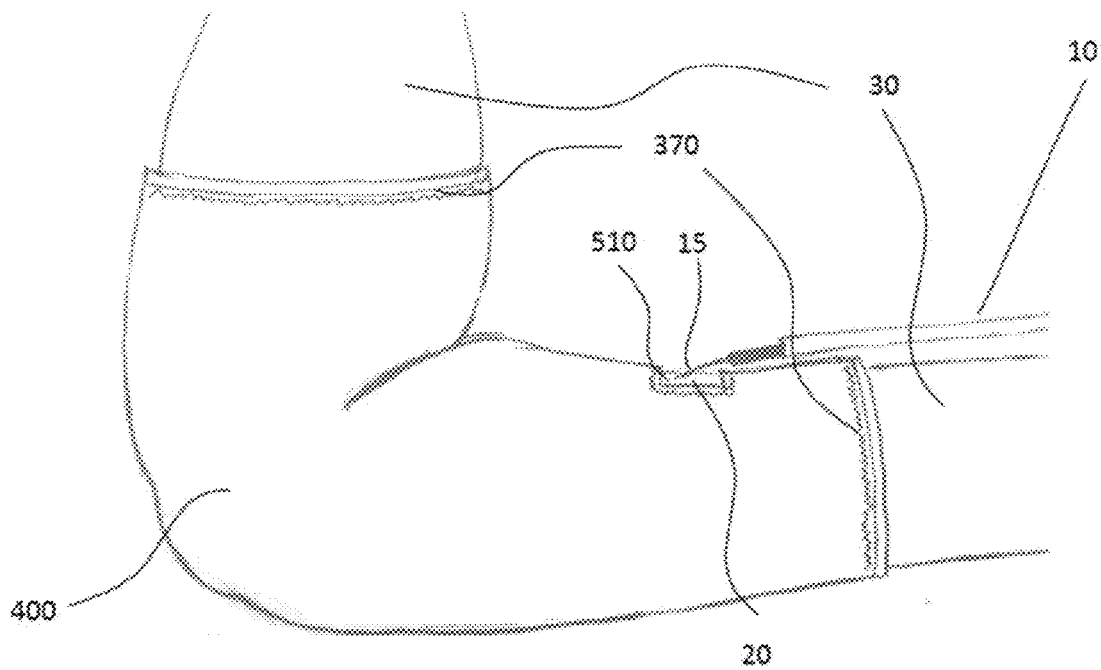
FIG. 5 shows the placement of an elastic fabric sleeve device on the arm of a patient according to a representative embodiment.
Figure 6:
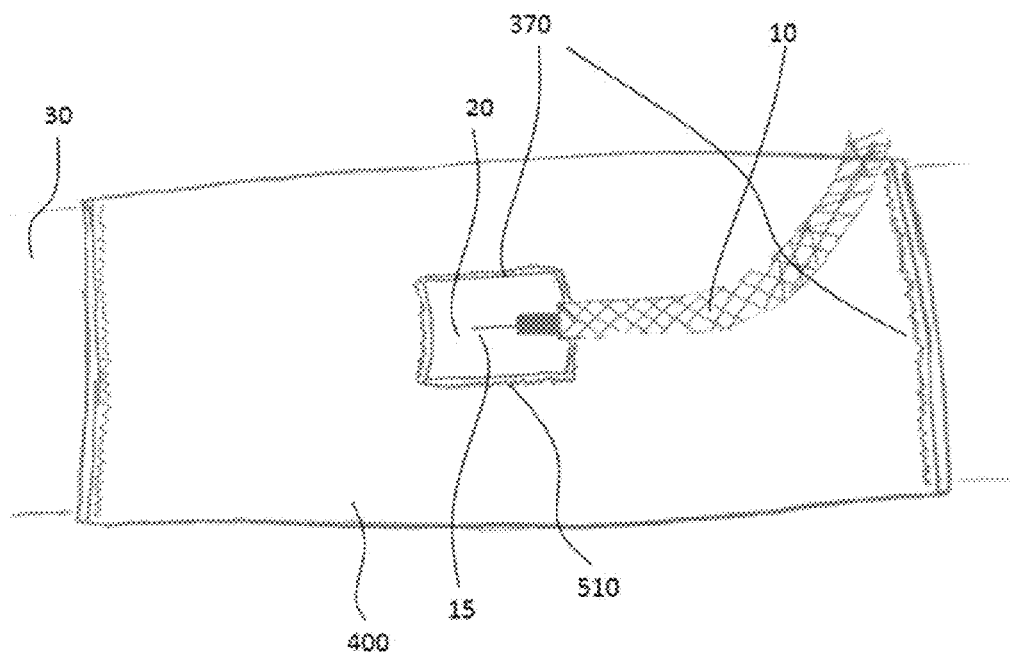
FIG. 6 shows a perspective view of the operation of an elastic fabric sleeve device according to a representative embodiment.
Figure 7:
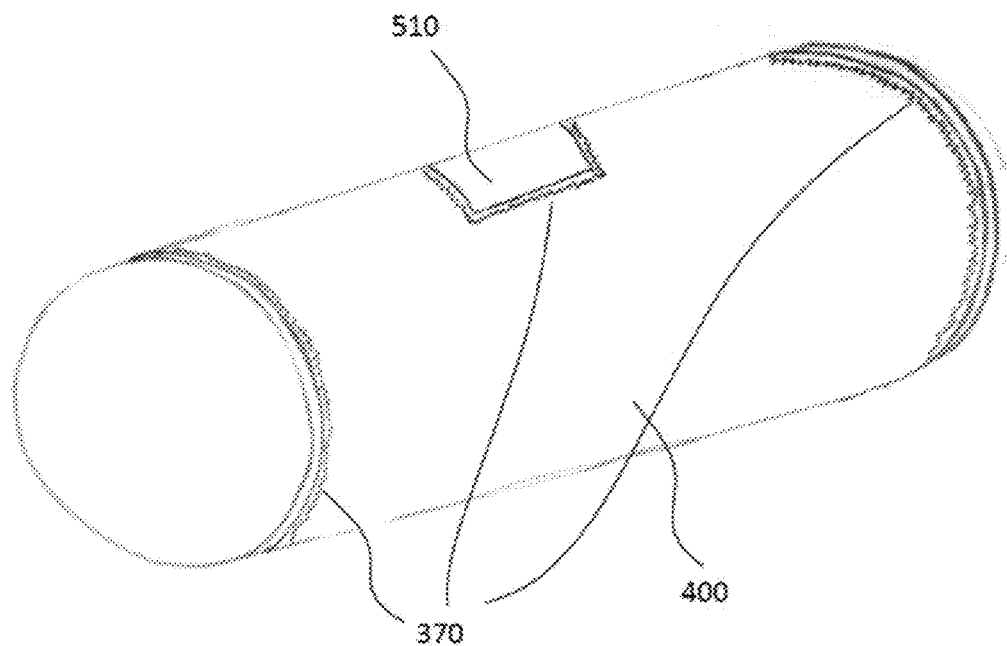
FIG. 7 shows a perspective view of an elastic fabric sleeve device according to a representative embodiment.

FIGS. 5, 6, 7 are representations of the elastic fabric 400 sleeve. FIG. 5 is an aerial representation of the elastic fabric 400 sleeve on a patient's arm 30 when, observed from above. The ends are sewn with elastic fabric stitches 370 and the elastic fabric 400 allows the sleeve to be stretched over the patient's arm 30 and then retreat back to a snug secure position on the arm. An intravenous catheter line 10 and an intravenous catheter tip 15 are shown to demonstrate the placement of the intravenous catheter in relation to the sleeve and the placement of the catheter within the skin opening 20 of the elastic fabric 400. The skin opening 20 is created by a rectangle cutout 510 of the elastic fabric 400 with elastic fabric stitches 370 around the ends. FIG. 7 is a representation of the elastic fabric 400 sleeve by itself. Elastic fabric stitches 370 are sewn are the ends and around the rectangle cutout 510. FIG. 5 is a representation of the elastic fabric 400 sleeve on a patient's arm 30 from the perspective of observing a neonate's bent elbow. The elastic fabric stitches 370 are at the ends of the sleeve and the top of the arm stretches the elastic fabric stitches 370 to a greater extent because that part of the arm is larger. The rectangle cutout 510 allows for the intravenous catheter tip 15 to enter the arm by creating a skin opening 20.

Figure 8:
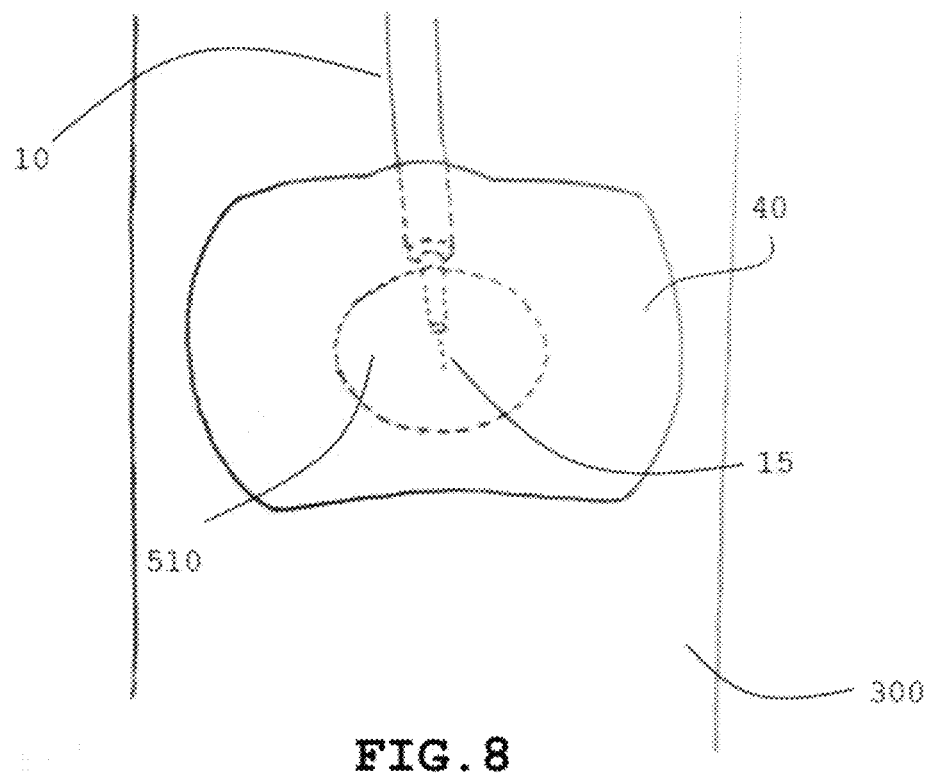
FIG. 8 shows a perspective view of an elastic fabric sleeve device and its operation with Tegaderm according to a representative embodiment.

Referring now to FIG. 8, a perspective view of the elastic fabric sleeve device and its operation with Tegaderm 40 according to a representative embodiment, the intravenous catheter tip 15 placed in the circle cutout 520 of the upper fabric assembly 300 is secured by Tegaderm 40.

Figure 9:
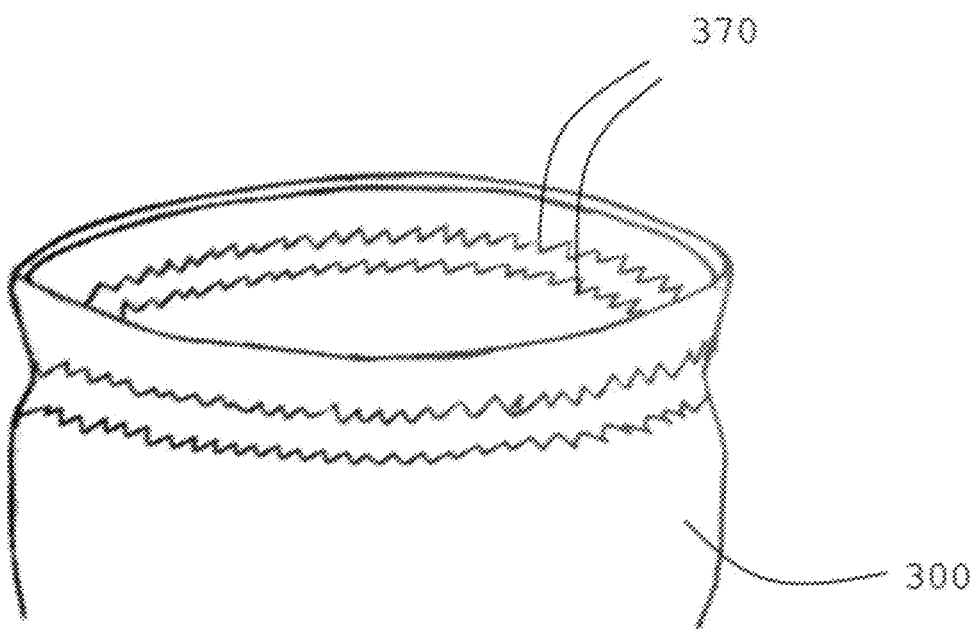
FIG. 9 shows a perspective view of an elastic band at the end of an elastic fabric sleeve device.

FIG. 9 shows a perspective view of an elastic band at one end of the upper fabric assembly 300. In this variation of the design, the upper fabric assembly 300 forms a tube so that in use the patient's arm is inside. The elastic fabric 400 is double hemmed with the stitch pattern described in FIG. 15 using elastic fabric stitches 370.

FIG. 10A-D shows the four possible fabric cutout shapes 500 in the elastic fabric 400. The rectangle cutout 510 is represented, in FIG. 7, a perspective view of the full sleeve, and FIG. 6, a perspective view of the full fabric assembly rested on a patient's arm. Alternate fabric cutout shapes 500 include a circle cutout 520, oval cutout 530, and a diamond cutout 540.

FIG. 11 represents a three-step zig-zag stitch pattern using elastic fabric stitches 370.

It should be appreciated that various sizes, dimensions, contours, rigidity, shapes, flexibility and materials of any of the components or portions of components in the various embodiments discussed throughout may be varied and utilized as desired or required. Similarly, locations and alignments of the various components may vary as desired or required.

It should be appreciated that any of the components or modules referred to with regards to any of the present invention embodiments discussed herein, may be integrally or separately formed with one another. Further, redundant functions or structures of the components or modules may be implemented.

It should be appreciated that the device and related components discussed herein may take on all shapes along the entire continual geometric spectrum of manipulation of x, y and z planes to provide and meet the anatomical and structural demands and operational requirements. Moreover, locations and alignments of the various components may vary as desired or required.

CONCLUSION

An embodiment provides a universal catheter securement device with the ability to stabilize intravenous catheters sans adhesive contact with the skin. Unlike other catheter securement devices, certain embodiments of this device minimize skin deformation, tearing, or damage to the epidermis barrier, and can provide a simple means of securing intravenous catheters.

What is claimed is:

1. A universal catheter securement device comprising:
an intravenous catheter board base to support a limb, and an upper fabric assembly to secure the limb and a catheter in place;
wherein the intravenous catheter board base comprising:
a cylindrical indentation which contacts the limb;
a foam padding on the cylindrical indentation for comfort;
cylindrical holes on two opposing sides of the intravenous catheter board base for securement of the upper fabric assembly to the intravenous catheter board base and for tightness adjustment; and
a first set of strips of hook fastener on underside of the intravenous catheter board base;
wherein the upper fabric assembly comprising:
an elastic fabric to encompass the limb around an insertion point of the catheter;
a sewing pattern of stitches for stretch ability;
a cutout hole at a center of the upper fabric assembly to provide an opening for access to insert the catheter; and
overlying securement flaps attached to one side of the upper fabric assembly via the sewing pattern of stitches, and also attached to other side of the upper fabric assembly via a second set of strips of hook fastener on the upper fabric assembly and a third set of strips of loop fastener on the overlying securement flaps, one of the overlying securement flaps which is positioned directly over the cutout hole in the upper fabric assembly.

2. The universal catheter securement device of claim 1, wherein the overlying, securement flaps further comprising: an outer layer made of the elastic fabric, and an inner layer made of a non-slip material.

3. The universal catheter securement device of claim 1, wherein the upper fabric assembly is fastened to the intravenous catheter board base via non-elastic bands that thread through eyelet-reinforced holes in the upper fabric assembly and connect to the cylindrical holes on one side of the intravenous catheter board base by tying to form a double band knot that forms a loop that permanently holds the upper fabric assembly to the intravenous catheter board base.

4. The universal catheter securement device of claim 3, wherein the upper fabric assembly is further attached to a fourth set of strips of loop fastener via elastic bands for tightness adjustment, the elastic bands of which hook through the cylindrical holes on other side of the intravenous catheter board base, and the fourth set of strips of loop fastener which attach to the first set of strips of hook fastener on the underside of the intravenous catheter board base.

5. The universal catheter securement device of claim 1, wherein the cutout hole in the upper fabric assembly is a circle shape.

6. The universal catheter securement device of claim 1, wherein the cutout hole in the upper fabric assembly is a rectangular shape.

* * * * *